United States Patent [19]

Moore

[11] Plant 4,031

[45] Mar. 29, 1977

[54] ROSE PLANT

[76] Inventor: Ralph S. Moore, 2519 E. Noble Ave., Visalia, Calif. 93277

[21] Appl. No.: 677,882

[22] Filed: Apr. 19, 1976

[51] Int. Cl.[2] ..... A01H 5/00

[52] U.S. Cl. ..... Plt./9

[58] Field of Search ..... Plt./9

*Primary Examiner*—Robert E. Bagwill

EXEMPLARY CLAIM

1. A new and distinct variety of miniature rose plant of hardy, dwarf, bushy, upright, much branched habit, essentially as illustrated and described, characterized by buds and flowers of a bright pink color resembling the Judy Fischer miniature rose (U.S. Plant Pat. No. 3,137) and resembling the Sheri Anne miniature rose (U.S. Plant Pat. No. 3,826) in size and form of bud and flower; and further characterized by a plant which is vigorous and compact, said plant being easy to propagate from cuttings, with medium small, disease resistant, glossy foliage, an abundance of bloom, with better than average keeping quality, with flowers borne singly or several to the stem in loose clusters.

1 Drawing Figure

1

The present invention relates to a new and distinct variety of hardy, dwarf, bush type rose plant of the miniature class; the variety being primarily characterized — as to novelty — by bright rose pink buds and flowers which in general color effect are similar to Judy Fischer (miniature — U.S. Plant Pat. No. 3,137).

The variety is further characterized by:

An abundance of bloom with flowers borne singly or several to stem in loose clusters.

Sweet fragrance.

A plant which is vigorous, of rounded upright shape and with glossy, medium — small foliage with pointed leaflets; the buds and flowers being similar in form and size to Sheri Anne (miniature — U.S. Plant Pat. No. 3,826).

The plant, which has a normal height of 12–14 inches, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at my nursery located at Visalia, Calif., under conditions of careful control and observation, as a cross between Rumba (Floribunda — U.S. Plant Pat. No. 1,919) as the seed parent and an un-named seedling (miniature — not patented) as the pollen parent.

Subsequent to origination of the variety I successfully asexually reproduced it, in my nursery located as aforesaid, by budding as well as by cuttings; the reproductions having run true in all respects.

The color photograph illustrates the variety, including foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy, dwarf, bushy; seedling; greenhouse; outdoors; cut flowers; garden decoration; potted plant.

Class: Miniature. Variety name: "Watercolor".

Flowers: Continuity; continuous — repeat bloom all season. Fragrance; sweet.

Flowers borne: Singly and several together (3 to 5) on sturdy, wiry, medium length stems.

2

Quantity of bloom: Abundant both outside and in greenhouse.

Bud: Peduncle — medium length; slender but sturdy; erect; medium green, sometimes tinted bronze (outdoors); hairs — may be some very short, very fine (fuzzy). Before calyx breaks; size — small. Form: medium long; pointed with few foliaceous appendages and few or no hairs on surface of bud; with foliaceous parts extending beyond the tip of the bud equal to one-half or less of its length. Color — medium green, occasionally tinted with bronze (outdoors). As calyx breaks, color — light red or pink; opens: same general color or lighter shade. Size — small.

Bloom: Size when fully open — small, averaging about 35 to 40 mm. Petalage — double 22–26 petals, arranged regularly. Form — full; high center at first, becoming more open in the center, with petals rolled loosely outward, and later at maturity open with petals folded at tips to give a pointed effect and rolled loosely outward and downward. Open flowers show yellow stamens.

Petals: Thick; satiny on inside and on outside surface. Shape — outside petals, broad lanceolate with acute tip; intermediate — broad lanceolate with acute tip; inside — lanceolate with acute tip.

Color: Newly opened flower from a plant grown in plastic greenhouse (March, 1976), Visalia, Calif.

*Outside petal.*—Outside surface — near Rose Madder 23 with both lighter and darker areas (or veining), and with small near white area at base; inside surface — pink, similar to Rose Madder 23/1 or lighter, shading into near white at base.

*Intermediate petal.*—Outside surface — similar to outside petal. Inside surface — similar to outside petal.

*Inner petal.*—Outside surface — same as intermediate petal; inside surface — same as intermediate petal. General color effect newly opened flowers — bright deep to medium pink. Three days open — color similar to newly opened flowers but lighter shade. Behavior — as flowers age the inside (upper) surface of petals (area exposed to sunlight) tend to deepen in color — often becoming quite red. Spent petals drop off. Flower longevity (October, 1975) — plant in pot 5–7 days or longer. Cut flowers at living room temperature 4–7 days.

Reproductive organs:

*Stamens.*—Abundant, arranged regularly about pistil.

*Filaments.*—Varying length, light yellow, fairly short.

*Anthers.*—Well formed; yellow.

*Pollen.*—Fair amount.

*Pistils.*—Average number.

*Styles.*—Fairly even; short to medium length; bunched; color — near white.

*Stigma.*—Nearly white,

*Ovaries.*—All enclosed in calyx.

*Hips.*—Several.

*Sepals.*—Permanent; spear shaped; recurved.

*Seed.*—Few.

Foliage:

*Leaves.*—Compound of five (sometimes three or seven) leaflets; abundant; medium small; leathery; glossy.

*Leaflets.*—Shape: broad lanceolate, nearly oval; apex acute; base rounded or rounded acute. Margin serrate. Color: medium green; new growth — reddish. Rachis: medium strength; upper side may have a few tiny short hairs and/or prickles, grooved, underside sparsely thorny with few or no tiny prickles.

*Stipules.*—Medium long; narrow to medium width medium length narrow points which turn out usually at about 45° or less.

Growth:

*Habit.*—Dwarf; bushy; upright; much branched.

*Growth.*—Free vigorous.

*Canes.*—Medium; slender; sturdy.

*Main stems.*—Color — medium green.

*Thorns.*—Few; usually small; straight, inclined slightly downward; color — brown. Prickles — none. Hairs — none.

*Branches.*—Color — medium green. Thorns — few; short length; slender; nearly straight inclined slightly downward. Medium to short oval base. Prickles — none. Hairs — none.

*New shoots.*—Color — reddish. Thorns — few; color — reddish; straight. Prickles — none. Hairs — none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, upright, much branched habit, essentially as illustrated and described, characterized by buds and flowers of a bright pink color resembling the Judy Fischer miniature rose (U.S. Plant Pat. No. 3,137) and resembling the Sheri Anne miniature rose (U.S. Plant Pat. No. 3,826) in size and form of bud and flower; and further characterized by a plant which is vigorous and compact, said plant being easy to propagate from cuttings, with medium small, disease resistant, glossy foliage, an abundance of bloom, with better than average keeping quality, with flowers borne singly or several to the stem in loose clusters.

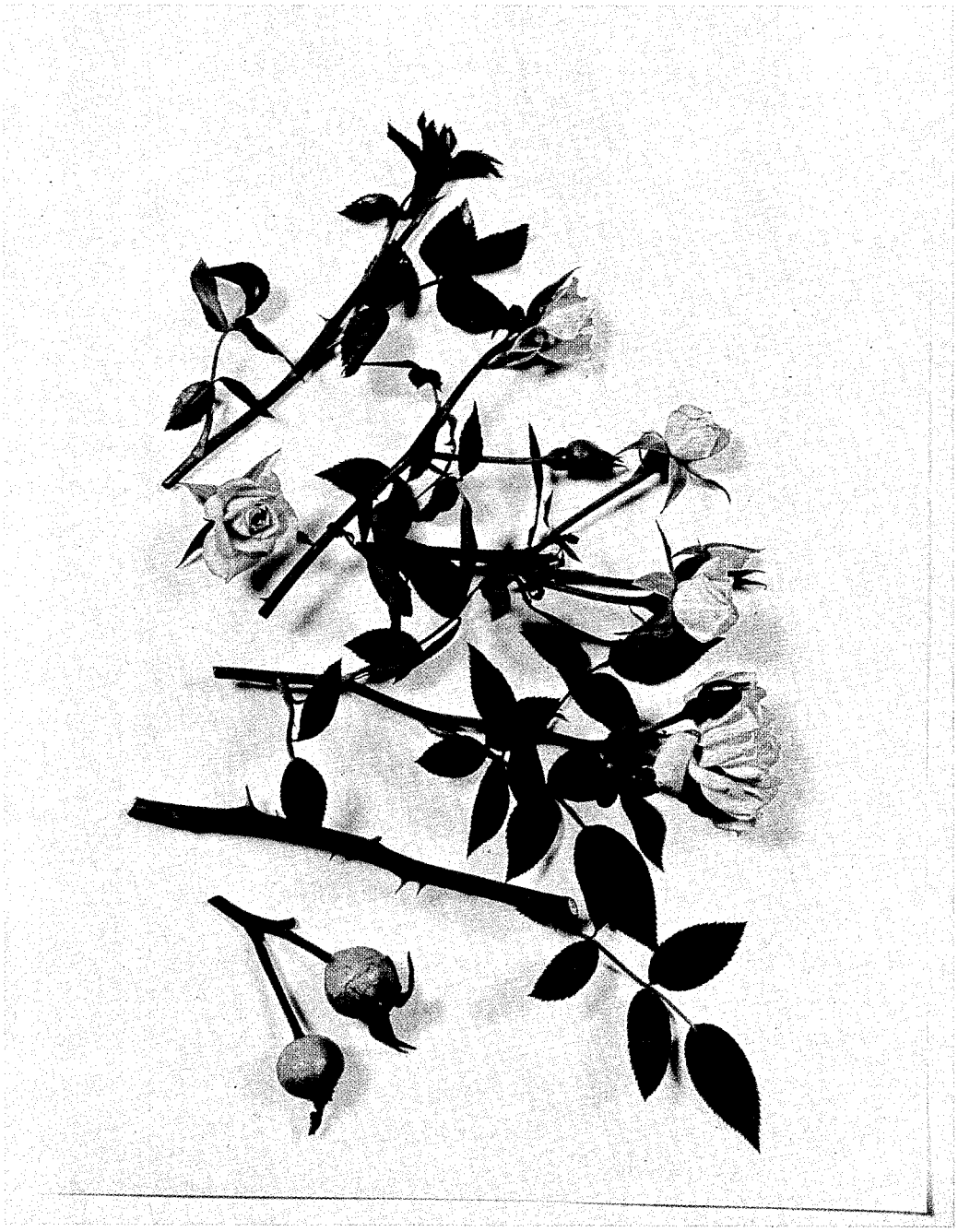

* * * * *